(12) United States Patent
Song et al.

(10) Patent No.: US 6,594,586 B1
(45) Date of Patent: Jul. 15, 2003

(54) INCORPORATION OF CONTEXTUAL INFORMATION IN OBJECT IDENTIFICATION

(75) Inventors: Xubo Song, Portland, OR (US); Yaser Abu-Mostafa, Pasadena, CA (US); Joseph Sill, Pasadena, CA (US); Harvey Kasdan, Sherman Oaks, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/182,601

(22) Filed: Oct. 28, 1998

Related U.S. Application Data

(60) Provisional application No. 60/063,690, filed on Oct. 28, 1997.

(51) Int. Cl.⁷ .............................. G06K 9/00; C12N 5/00; G01N 33/53
(52) U.S. Cl. ........................ 702/19; 382/133; 382/134; 435/235; 436/800
(58) Field of Search ........................... 435/325; 702/19; 436/800; 382/133, 134

(56) References Cited

U.S. PATENT DOCUMENTS

| 4,538,299 A | | 8/1985 | DeForest |
| 5,123,055 A | * | 6/1992 | Kasdan ........................... 382/6 |
| 5,343,538 A | | 8/1994 | Kasdan |
| 5,436,978 A | * | 7/1995 | Kasdan ........................... 382/6 |
| 5,733,721 A | * | 3/1998 | Hemstreet, III et al. ........ 435/6 |

OTHER PUBLICATIONS

Database GenBank accesion No. Q74185, Donnelly et al. May 31, 1995, See sequence alignment.*
Database GenEmbl accesion No. AB008889, Otsuka et al., Feb. 13, 1999. See sequence alignment.*

* cited by examiner

*Primary Examiner*—Michael Borin
(74) *Attorney, Agent, or Firm*—Fish & Richardson P.C.

(57) ABSTRACT

Analysis of white blood cells is carried out by first analyzing the sample using image processing to obtain a no-context estimate of each cell's content. Then, a post processing operation is carried out to refine the estimate to include information about neighboring white blood cells. The estimate is refined to take into account the identity of the neighboring cells.

8 Claims, 2 Drawing Sheets

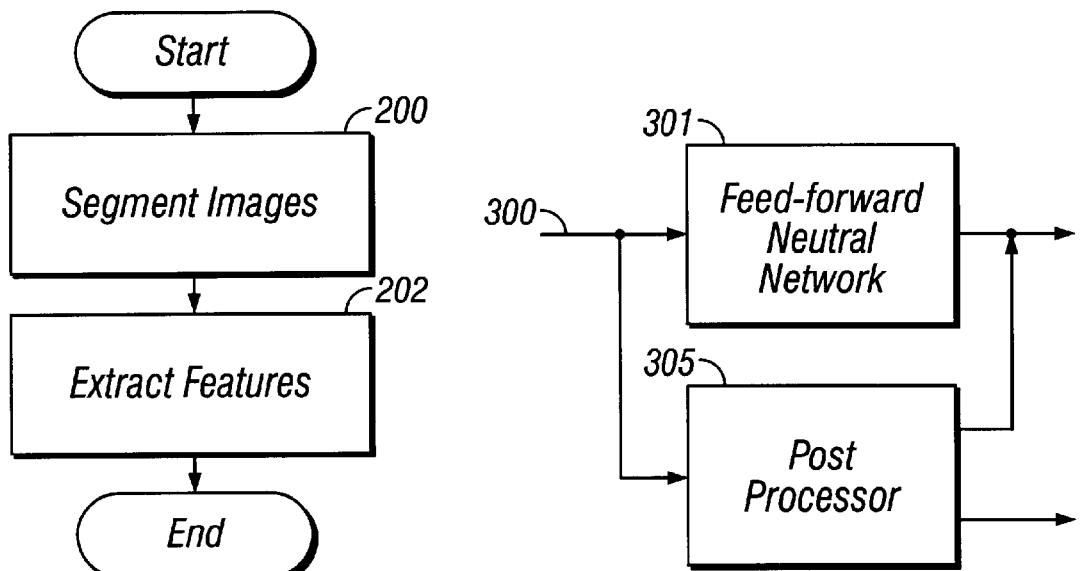
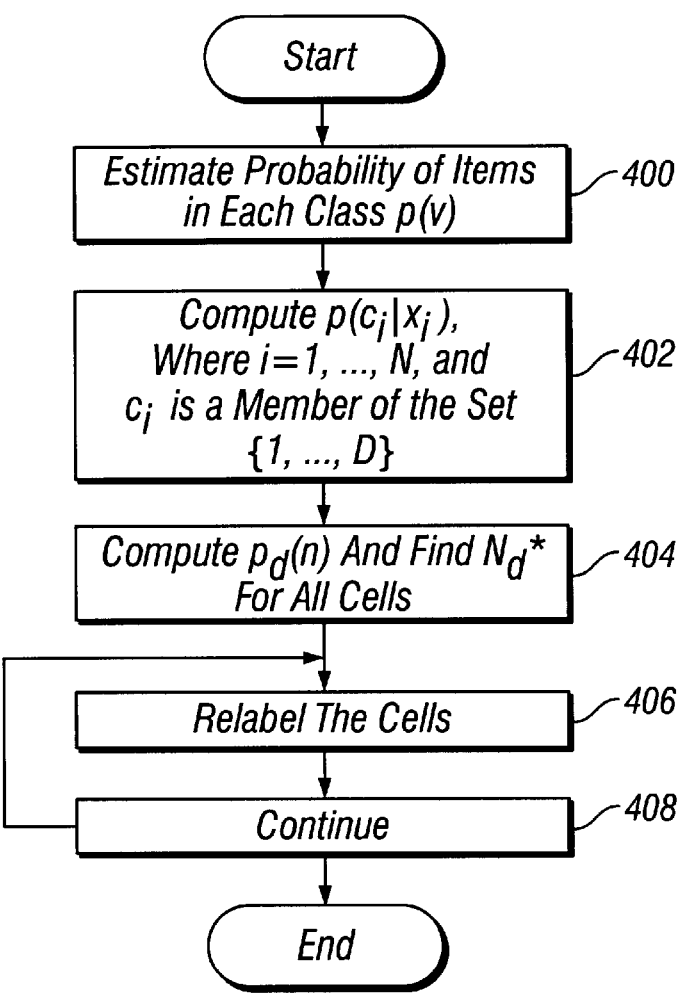

INCORPORATION OF CONTEXTUAL INFORMATION IN OBJECT IDENTIFICATION

CROSS REFERENCE TO RELATED APPLICATIONS

Priority to provisional U.S. patent application Ser. No. 60/063,690, filed Oct. 28, 1997 is claimed.

FIELD OF THE INVENTION

The invention relates to techniques of identifying and classifying objects. More specifically, the present system describes using contextual information to improve statistical accuracy.

BACKGROUND

A common assumption made in the field of machine learning is that the examples are drawn independently from some joint input-output distribution.

Classical statistics begins with an assumption of a population distribution. Tiat population distribution describes how some attribute varies over a set of entities. The goal is to obtain information about the population distribution by sampling or by some other real world technique. It is often impractical to evaluate the parameters exactly. Therefore, one attempts, using the techniques of statistics, to obtain as much information as one can based on experimental evidence. Then all of the parameters can be viewed a coordinates of a single vector often called x . The value of x is fixed, but there is uncertainty about its value.

The population often has a distribution. For example, if the population has a Gaussian distribution, the parameters may have a mean value $\mu$ and a standard deviation $\Sigma$.

The Bayesian approach models the population by considering elements of the population to be randomly selected from a class of populations. Each class of the population is characterized by parameters that are under investigation. Bayesian analysis considers two parameters x and y. Bayesian analysis is largely an effort at determining the probability for the occurrence of the event y=$\beta$ conditioned by the fact that x=$\alpha$ has occurred. During N trials the event x=$\alpha$ occurs $n_x(\alpha)$ times. The joint effect x=$\alpha$ and y=$\beta$ occurs $n_{xy}(\alpha, \beta)$ times.

The usual Bayesian approach assumes the distribution for x by looking at the trials for x. Hence, Bayesian analysis considers the trials in which x=$\alpha$. Once the random sampling processes are obtained, the notion of the random sampling process is extended by assuming that the class $x_i$: 1 is less than or equal to I; is conditionally independent. Each of the $x_i$ have the same conditional distribution. This is because each of the $x_i$ are defined through the same random parameter x. While the events x and y are independent, both have the same conditional probabilities. Hence, the conditional probability that y=$\beta$ given that x=$\alpha$ is independent of $\alpha$. This means that $$P_{x|y}(\alpha|\beta) = \frac{P_{x|y}(\beta|\alpha)P_x(\alpha)}{P_y(\beta)}$$

where the left part is the conditional probability that y=$\beta$ given that x=$\alpha$, the right part is the conditional probability that x=$\alpha$ given that y=$\beta$, $p_x(\alpha)$ is the probability of $\alpha$ and $p_x(\beta)$ is the probability of $\beta$.

Bayesian analysis is often used in estimator design. For instance, the conditional probability of a received message may be known and the conditional probability of the transmitted message is to be obtained. Bayesian analysis requires that the examples are drawn independently from the joint input/output distribution, as described above.

There are cases, however, where this no context assumption is not valid. One application where the independence assumption does not hold is the identification of white blood cell images. Abnormal cells are much more likely to appear in bunches than in isolation. Specifically, in a sample of several hundred cells, it is more likely to find either no abnormal cells or many abnormal cells than it is to find just a few. More generally, certain random processes are subject to "aliasing" whereby they occur in clumps.

SUMMARY OF THE INVENTION

The present specification describes pattern classification in situations where an independence assumption is not necessarily correct. In such cases, the probability of identity of an object may be dependent on the identities of the accompanying objects. Those accompanying objects which provides the contextual information.

The techniques take into consideration the joint distribution of all the classes, and uses the joint distribution to adjust the object-by-object classification.

This method can be used in a number of settings. For example, the classification of white blood cells is improved by the use of contextual information.

BRIEF DESCRIPTION OF THE DRAWINGS

These and other aspects of the invention will now be described with reference to the attached drawings, in which:

FIG. 2 shows a flowchart of no-context classification;

FIG. 3 shows a device for carrying out this operation; and

FIG. 4 shows the post processing operation to include contextual information.

DETAILED DESCRIPTION

Figure 1:
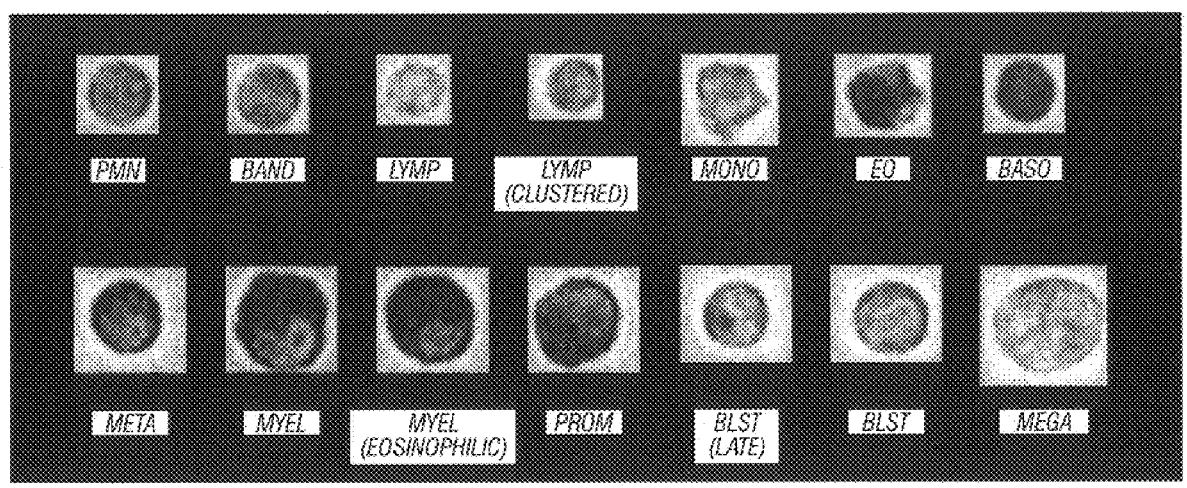
FIG. 1 shows exemplary views of different kinds of white blood cells.

The objects are described herein by a vector that defines their probabilistic characteristics taken as having feature vectors.

The feature vector is defined as $x_i$. The feature vector is be classified into one of a number of classes. The classification of a given feature vector $x_i$ is defined as $c_i=c(x_i)$, I . . . 1 to N, where N is the total number of objects and hence the total number of feature vectors. The classification $c_i$ is a member of the set $\{1, \ldots, D\}$, where D is the total number of classes.

For example, if one considers ten samples of blood, possible feature vectors could include the different types of white blood cells.

Leukocyte analysis is an important routine laboratory examinations. Leukocyte classification aids in clinical diagnosis because the relative percentage composition of the blood leukocytes changes in various physiological and pathological conditions. An estimate of the percentage of each class present in a blood sample conveys information which is pertinent to the hematological diagnosis.

Typical commercial differential white blood cell ("WBC") counting systems are designed to identify five major mature cell types. Blood samples, however, may also contain other types of cells, i.e., immature cells. These cells occur infrequently in normal specimens. Most commercial systems will simply indicate the presence of these cells because such systems cannot be individually identified. These cell types that relate to the production rate and maturation of new cells. The present inventors, however, believe that these are important indicators of hematological disorders.

The preferred system differentiates up to fourteen WBC types. This includes the five major mature types: segmented neutrophils, lymphocytes, monocytes, eosinophils, and basophils; and the immature types: bands (unsegmented neutrophils), metamyelocytes, myelocytes, promyelocytes, blasts, and variant lymphocytes; as well as nucleated red blood cells and artifacts. Differential counts are made based on the cell classifications, which further leads to diagnosis or prognosis. The fourteen different cell types to be identified are shown in FIG. 1.

According to Bayes rule, where $p(c|x)$ is the probability of c if x is given, $p(c)$ is the probability of c and $p(x)$ is the probability of x.

$$p(c|x) = \frac{p(x|c)p(c)}{p(x)}$$

That is, the probability of c given x, is the probability of x given c, times the probability of c divided by the probability of x.

This is the no-context rule, correct only when the entire class has a random and flat probabilistic value. In white blood cell analysis, as described above, the probability of any sample being any c is dependent on the rest of the neighboring population. In context, each of the classes of this system can have a different probabilistic value. Therefore, the "with context" a posteriori probability of the class label of all the objects assumes value $C_1, C_2, \ldots, C_N$, given all the feature vectors, is $$p(c_1, c_2, \ldots, c_N | x_1, x_2, \ldots, x_N) = \qquad (1)$$

$$\frac{p(x_1, x_2, \ldots, x_N | c_1, c_2, \ldots, c_N)p(c_1, c_2, \ldots, c_N)}{p(x_1, x_2, \ldots, x_N)}$$

The feature distribution of a given class is independent of the feature distributions of other classes, i.e., $$p(x_1 x_2, \ldots, x_N | c_1, c_2, \ldots, c_N) = p(x_1 | c_1) \ldots p(x_N | c_N)$$

This Equation (1) can be rewritten as $$p(c_1, c_2, \ldots, c_N | x_1, x_2, \ldots, x_N) = \qquad (2)$$

$$\frac{p(x_1 | c_1) \ldots p(x_N | c_N)p(c_1, c_2, \ldots, c_N)}{p(x_1, x_2, \ldots, x_N)} =$$

$$\frac{p(c_1 | x_1) \ldots p(c_N | x_N)p(x_1) \ldots p(x_N)p(c_1, c_2, \ldots, c_N)}{p(c_1) \ldots p(c_N)p(x_1, x_2, \ldots, x_N)}$$

Where $p(c_i|x_i)$ is the "no context" object-by-object Bayesian a posteriori probability, $p(c_i)$ is the a priori probability of the classes, $p(x_i)$ is the a priori probability of the features. The features $(x_1, x_2, \ldots, x_N)$ are given. Hence their probabilities $p(x_1, x_2, \ldots, x_N)$ and $p(x_i)$ are constant. Therefore $$p(c_1, \ldots, c_N | X_i \ldots X_n) \propto p(c_1 | x_1) \ldots p(c_N | x_N) \frac{p(c_1, \ldots, c_N)}{p(c_1) \ldots p(c_N)}$$

where

The description made herein is for the application of object $$= p(c_1 | x_1) \ldots p(c_N | x_N)p(c_1, c_2, \ldots, c_N) \qquad (3)$$

$$p(c_1, c_2, \ldots, c_N) \equiv \frac{p(c_1, c_2, \ldots, c_N)}{p(c_1) \ldots p(c_N)}$$

classification. Object classification determines the count in each class, rather than the particular ordering or numbering of the objects. As a result, $P(c_1, c_2, \ldots, c_N)$ is only a function of the count in each class.

Let $N_d$ be the count in class d, and $u_d$ is the percentage of objects in the class, $=N_d/N$, for $d=1 \ldots, D$, then:

$$p(c_1, c_2, \ldots, c_N) = \frac{p(c_1, c_2, \ldots, c_N)}{p(c_1) \ldots p(c_N)} = \frac{N! p(v_1, v_2, \ldots, v_D)}{N_1! \ldots N_D! P_1^{Nv_1} \ldots P_D^{N_{VD}}} \qquad (4)$$

where $P_d$ is the prior distribution of class d, for $d=1, \ldots D$.

$$\sum_{D=1}^{D} Nd = N \text{ and } \sum_{D=1}^{D} vd = 1.$$

$$= p(v_1, \ldots, v_D)$$

$$= p(v_1, \ldots, v_D)$$

$$(c_1, c_2, \ldots, c_N)$$

The decision would then become $$(c_1, c_2, \ldots, c_n) = \operatorname{argmax} p(c_1, c_2 \ldots, c_N | x_1, x_2, \ldots x_N)$$

$$(c_1, c_2, \ldots, c_n)$$

Implementing this decision rule requires computing and comparing $D^N$ terms to solve Equation 5. In our case of white blood cell recognition, D=14 and N is typically around 600, requiring $600^{14} \approx 8 \times 10^{38}$ terms—an unmanageable number of calculations.

The technique disclosed uses a simplification to avoid the massive computation. Instead of considering all the classes all at once, one class is considered at a time. Take the class d for example.

Defining $p^d_i$ to denote the probability that d is the classification for group $x_i$, $=P(c_i=d|x_i)$, $I=1, \ldots, N$. We order the $P^d_1, P^d_2, \ldots, P^d_N$'s in a descending manner dependent on I, such that $$p_1^d >= p_2^d >= \ldots >= p_N^d \qquad (6)$$

Then, the probability that there are n cells belonging to class d is $$P_d(n) = p_1^d \ldots p_n^d \cdot (1-p_{n+1}^d) \ldots (1-p_N^d) p\left(v_1, \ldots, v_d = \frac{n}{N}, \ldots, v_D\right)$$

The $P_d(n)$'s can be computed recursively.
First, we calculate $P_d(0)$:

$$P_d(0) = (1-p_1^d) \ldots (1-p_N^d) p\left(v_1, \ldots, v_d = \frac{0}{N}, \ldots, v_D\right)$$

Then, the other values are calculated from Pd(0)

$$P_d(n+1) = P_d(n) \frac{p_{n+1}^d p\left(v_1, \ldots, v_d = \frac{n+1}{N}, \ldots, v_D\right)}{1 - p_{n+1}^d) p\left(v_1, \ldots, v_d = \frac{n}{N}, \ldots, v_D\right)}$$

This way all the $P_d(n)$'s computed from only N terms.
The value $n = n^*$ that maximizes $P_d(n)$, $n=1, \ldots, N$ is selected. Then all the objects that rank highest—the top $n^*$ in Equation 6—are classified into class d. This can be carried out in a similar way for all the classes.
Importantly, $$p(v_1, \ldots, v_D) = \frac{N! p(v_1, v_2, \ldots, v_D)}{N_1! \ldots N_D! P_1^{Nv_1} \ldots P_D^{Nv_D}}$$

is simply a count of overall probability of any particular white blood cell. This count can be estimated from a database of known cells.

Application to White Blood Cell Recognition

The data was provided by IRIS, Inc. (International Remote Imaging Systems, Inc., Chatsworth, Calif.). Blood specimens were collected from local patients at Harbor UCLA Medical Center, then dyed with Basic Orange 21 metachromatic dye supravital stain. The specimens were then passed through a flow microscopic imaging and image processing instrument, where the blood cell images were captured. Each image has a single cell with full color. There are typically 600 images from each specimen, so N–600.The cell recognition system categorizes the cells based on the images.

The size of cell images are automatically tailored according to the size of the cell in the images. Images containing larger cells had bigger sizes than those with small cells. The range varied from 20×20 to 40×40 pixels. The average size is about 25×25 pixels.

The image processing operation is described with reference to the flowchart of FIG. 2, in which steps 200 and 202 represent the cell-by-cell classification of each cell. Each image containing a single cell is segmented in order to emphasize the interior of the cell relative to the image. At step 202 the features are extracted. These features which are extracted include, for example, size, shape, color and texture. The color image is decomposed into its three primary colors, red, green and blue. The portions of red, green and blue set the overall color that is used for identification. Since the cells fall into certain categories, one of the processing features used determines red and blue information. The first part of the operation determines a red-blue distribution. This is the pixel-by-pixel value of log(red)—log(blue) which forms the distribution for the pixels in the cell interior. The red distribution from pixels in the cell interior can also be obtained. The preferred featured information, including the size, shape, color and texture, are described in more detail in Table 1.

TABLE 1

Features Extracted from Cell Images

| feature number | feature description |
|---|---|
| 1 | cell area |
| 2 | number of pixels on cell edge |
| 3 | the 4th quantile of red-blue distribution |
| 4 | the 4th quantile of green-red distribution |
| 5 | the median of red-blue distribution |
| 6 | the median of green-red distribution |
| 7 | the median of blue-green distribution |
| 8 | the standard deviation of red-blue distribution |
| 9 | the standard deviation of green-red distribution |
| 10 | the standard deviation of blue-green distribution |
| 11 | the 4th quantile of red distribution |
| 12 | the 4th quantile of green distribution |
| 13 | the 4th quantile of blue distribution |
| 14 | the median of red distribution |
| 15 | the median of green distribution |
| 16 | the median of blue distribution |
| 17 | the standard deviation of red distribution |
| 18 | the standard deviation of green distribution |
| 19 | the standard deviation of blue distribution |
| 20 | the standard deviation of distance from the edge to the mass center |

The features are analyzed using a neural network shown in FIG. 3. A nonlinear feed-forward neural network 301 has 20 inputs, 15 hidden units with sigmoid transfer functions, and 14 sigmoid output units. This architecture is chosen through cross-validation. A cross-entropy error function is used in order to give the output a probability interpretation.

Denoting the input feature vector as x, the network outputs a D-dimensional vector, where D=14 in this embodiment $p = \{p(d|x)\}, d = 1, \ldots, D$, where $p(d|x)$ is the probability that a cell belongs to class d, given the presence of feature x. The decision made at this stage is $$d(x) = \arg\max p(d|x)$$

Once the cell-by-cell classification is made, the present system uses the post processor 305 to refine this cell-by-cell classification using the contextual information.

Each of these features identified in step 202 becomes a feature number which is used to help identify the cell and where it belongs relative to the other cells. Comparisons and associations are also used to compare the cell under interest with other cells in the same specimen. According to this embodiment, the cell is more likely to assume a certain identity if the company it keeps supports that identity.

Again, the "no-context" cell-by-cell decision is only based on the features presented by a cell, without looking at any other cells. However, a cell is more likely to assume a certain identity if the surrounding cells support that identity.

For instance, the difference between lymphocyte and blast can be very subtle sometimes, especially when the cell is large. A large unusual mononuclear cell with the characteristics of both blast and lymphocyte is more likely to be a blast if it is surrounded by or accompanied by other abnormal cells or abnormal distribution of the cells.

This type of analysis fits within the framework presented above for incorporating contextual information. Hence, the image 300 is also coupled to post processor 305. The post-processing draw on the mathematical framework above. The overall technique proceeds according to the basic probability flowchart of FIG. 4.

At step 400, the algorithm estimates $P(v, , \ldots v_D)$ from the database for each of $d=1 \ldots D$. Since $N_d$ is the percentage of objects in class D, the numbers can in fact be estimated.

At step 402, the object-by-object no context, a posteriori probability $p(c_i|x_i)$ is computed for all objects $I=1 \ldots N$, $C \in 1 \ldots D$. This uses known statistical techniques described in equation (2). Now all terms for equation 7 have been calculated.

At step 404, the probability Pd(n) that a cell belongs to class D is calculated using equation (7) using the terms calculated in steps 400 and 402. The maximum value $n_d^*$ for all D's is also determined. The cells are re-labeled appropriately at step 406. This corresponds to the equation 6.

Step 406 is continued until the re-labeling process converges, shown as step 408.

The technique described above for combining contextual information is used as the post-processing step using post processor 405 for the cell-by-cell decision process. The final output information then is post-processed using techniques described above.

Empirical Testing

The techniques described herein have been intensively tested at IRIS, Inc. on the specimens obtained at Harbor UCLA medical center. The performances with or without using contextual information on blood samples from 200 specimens (13,200 cells) were tested. In 50% of the cases, a false alarm would have occurred had context not been used. Most cells are correctly classified, but a few are incorrectly labeled as immature cells, which raises a flag for the doctors. Change of the classification of the specimen to abnormal requires the expert intervention before the false alarm is eliminated, and it may cause unnecessary worry. When context is applied, the false alarms for most of the specimens were eliminated.

The technique described can be generalized to a number of domains where contextual information plays an essential role, such as speech recognition, character recognition, and other medical diagnosis regimes. In speech recognition and character recognition, the identity of a word depends on the identities of neighboring words. Context plays a key role, much as it does in the recognition of blood cells.

Although only a few embodiments have been described in detail above, other embodiments are contemplated by the inventor and are intended to be encompassed within the following claims. In addition, other modifications are contemplated and are also intended to be covered.

What is claimed is:

1. A method of classifying an identity of a cell, the method comprising:

(a) generating a first no-context estimate of an identity of a cell in a specimen;

(b) generating a plurality of no-context estimates of a plurality of other cells in the specimen;

(c) generating one or more with-context estimates of the identity of the cell comprising using the plurality of no-context estimates about the plurality of other cells in the specimen to modify the first no-context estimate of the cell; and (d) identifying the cell as belonging to a particular class based on the one or more with-context estimates, thereby classifying an identity of the cell, wherein generating the no-context estimate comprises applying a statistical approach to the cell to be identified, and wherein generating the one or more with-context estimates comprises determining a probability of a cell belonging to a particular class given features of other cells in the specimen.

2. The method of claim 1 wherein the statistical approach comprises applying a Bayes' rule statistical approach.

3. The method of claim 1, wherein identifying the cell as belonging to a particular class based on one or more with-context estimates comprises determining a probability of a cell belonging to any of a plurality of classes, and selecting a maximum probability as representing a cell's identity.

4. The method of claim 1, wherein generating the one or more with-context estimates comprises:

determining a probability of n cells belonging to a particular class, where n equals 1; and recursively using the determined probability to identify a class with a highest probability by incrementing n from 2 to N, where N is a number of cells to be classified.

5. A method of classifying a white blood cell, the method comprising:

(a) generating a first no-context estimate of an identity of a cell in a specimen;

(b) generating a plurality of no-context estimates of a plurality of other cells in the specimen;

(c) generating one or more with-context estimates of the identity of the cell comprising using the plurality of no-context estimates about the plurality of other cells in the specimen to modify the first no-context estimate of the cell; and (d) identifying the cell as belonging to a particular class of white blood cells based on the one or more with-context estimates, thereby classifying the white blood cell, wherein generating the no-context estimate comprises applying a statistical approach to the cell to be identified, and wherein generating the one or more with-context estimates comprises determining a probability of a cell belonging to a particular class of white blood cells given features of other cells in the specimen.

6. The method of claim 5 wherein the statistical approach comprises applying a Bayes' rule statistical approach.

7. The method of claim 5 wherein identifying the cell as belonging to a particular class of white blood cells based on one or more with-context estimates comprises determining a probability of a cell belonging to any of a plurality of classes of white blood cells, and selecting a maximum probability as representing a cell's identity.

8. The method of claim 5 wherein generating the one or more with-context estimates comprises:

determining a probability of n cells belonging to a particular class of white blood cells, where n equals 1; and recursively using the determined probability to identify a class with a highest probability by incrementing n from 2 to N, where N is a number of cells to be classified.

* * * * *